United States Patent [19]

Hall

[11] 4,225,672

[45] Sep. 30, 1980

[54] METHOD FOR PRODUCING MALTOOLIGOSACCHARIDE GLYCOSIDES

[76] Inventor: Leo M. Hall, 406 Devon Dr., Homewood, Ala. 35209

[21] Appl. No.: 15,681

[22] Filed: Feb. 27, 1979

[51] Int. Cl.$^2$ .............................................. C12P 19/44
[52] U.S. Cl. ...................................... 435/74; 435/15; 435/22; 435/193; 435/832; 435/837; 435/852
[58] Field of Search ............................... 435/74, 22, 15

[56] References Cited

U.S. PATENT DOCUMENTS

4,102,747  7/1978  Driscoll et al. ......................... 435/22

OTHER PUBLICATIONS

Wallenfels et al., Carbohydrate Research, 61, 359-368 (1978).

Primary Examiner—Lionel M. Shapiro
Attorney, Agent, or Firm—Edward A. Figg; Robert E. Hartenberger

[57] ABSTRACT

Disclosed herein is a method for producing maltooligosaccharide glycosides in substantially pure form which includes the steps of incubating a glucosyl donor and a glucosyl acceptor in the presence of a glucanotransferase enzyme under transglycosylating conditions and separating the maltooligosaccharide glycoside from the reaction mixture.

8 Claims, No Drawings

METHOD FOR PRODUCING MALTOOLIGOSACCHARIDE GLYCOSIDES

BACKGROUND OF THE INVENTION

1. Field of the Invention

The present invention relates to a method for the preparation of maltooligosaccharide glycoside derivatives of p-nitrophenol, 4-methylumbelliferone and other chromogenic or fluorogenic aglycones. More particularly, the invention relates to an enzymatic method for the preparation of suitable chromogenic or fluorogenic maltooligosaccharide glycoside derivatives for use, for example, as substrates for the determination of amylase activity.

2. Description of the Prior Art

Heretofore, only processes involving organic synthetic reactions have been used for the preparation for the chromogenic or fluorogenic derivatives of oligosaccharides suitable for use as substrates for the determination of amylase activity. (Jansen and Rawlins, Nature 182, 525, 1958; and Driscoll, Richard C., et al., U.S. Pat. No. 4,102,747. In these methods, the yield of desired derivative, its suitability as an amylase substrate, or its low purity have prevented significant improvements in several analytical systems for the determination of amylase activity which would be possible if such substrates were available in a commercially and technically acceptable fashion.

Amylase assay procedures have been developed which utilize substrates such as starch, glycogen, dextrin, and oligosaccharides. However, the use of such substrates has suffered from the disadvantage that endogenous glucose present in the reaction sample sometimes causes interference with the results of the assay. Procedures utilizing these substrates have been developed which overcome the glucose interference problem, however the reaction sequences involved in these procedures are complicated and often quite costly.

The Driscoll, et al. procedure cited above overcomes the problems of glucose interference and high cost, however, heretofore no satisfactory procedure has been reported for producing the maltooligosaccharide glycoside substrate in a commercially feasible manner. The availability of defined chromogenic or fluorogenic derivatives of maltooligosaccharide glycosides will permit significant improvements in the Driscoll et al. method for the determination of amylase activity according to the following reactions in which the substrate, p-nitrophenyl-α-D-maltoheptaoside is used for illustrative purposes only:

(1)

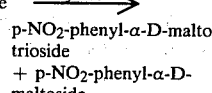

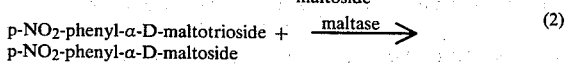

(2)

p-NO₂-phenol + glucose

The rate of formation of p-nitrophenol, once zero-order kinetics is established for equation (2) is directly proportional to the amylase present in the sample. p-Nitrophenol may be monitored spectropholometrically by its absorbance at 405 nm.

In a similar fashion, amylase activity may be determined using a fluorogenic substrate such as 4-methylumbelliferyl-α-D-maltoheptaoside. In such a case, the rate of increase in fluorescence is proportional to the amylase activity.

The organic synthetic reactions heretofore used for producing chromogenic and fluorogenic substrates have produced substrates having both α and β configurations. Accordingly, because in the Driscoll et al. method the use of substrates having the β configuration requires the use of β glucosidase as an additional reactant, there is a need for a method for producing substrates having either the α configuration or the β configuration in substantially pure form. The availability of substrates with the β-anomeric configuration would provide improvements in the Driscoll et al. method for the measurement of amylase activity according to the following reactions in which the substrate, p-nitrophenol-β-D-maltoheptaoside is used for illustrative purposes only:

(1)

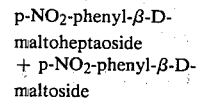

(2)

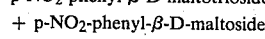

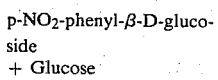

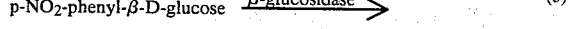

(3)

p-NO₂ phenol + glucose

The rate of formation of p-nitrophenol, once zero-order kinetics has been established, for reaction (3) is directly proportional to the amylase activity of the sample. p-Nitrophenol may be monitored by its absorbance at 405 nm spectrophotometrically. In a similar fashion, amylase activity can be determined using a fluorogenic substrate such as 4-methylumbelliferyl-β-D-maltoheptaoside. In such a case, the rate of increase in the fluorescence is proportional to the amylase activity.

From the foregong discussion, it can be readily seen that the analytical methods employing chromogenic or fluorogenic substrates for the measurements of amylase activity represent decided improvements in existing technology for the measurment of the enzyme. To render these procedures useful for routine use, there is a need for methods for producing the α and β-maltooligosaccharide glycoside derivatives in substantially pure form and high yield.

The well known glucanotransferase (E.C.2.4.1.19) of *Bacillus macerans* has primarily been used for the production of cyclic dextrins from starch. (Tilden and Hudson; J. Bact., 43, 727–744, 1942, J. Am. Chem. Soc., 61, 2900–2902, 1939). The use of the enzyme for the transfer of glucosyl groups from cyclic dextrins to suitable acceptors such as D-glucose, D-maltooligosaccharides, and D-glucosides, has been reported (French, et al; J. Am. Chem. Soc. 76 2387–2390, 1954). Also, in British Pat. No. 1,442,480, is reported a method for producing oligoglucoylfructose utilizing a glucanotransferase enzyme isolated from a strain of *Bacillus stearothermophilus*. A similar enzyme has been isolated from *Klebsiella pneumoniae* (Bender, Arch. Microbiol., 111, 271–282, 1977) and from *Bacillus megaterium* (Kitahata, et al., Proc. Symposium on Amylase, Volume 7, 61–68, 1972). Heretofore, the use of glucano-transferase enzymes for the enzymatic synthesis of substantially pure α and β p-nitrophenyl or 4-methylumbelliferyl maltooligosaccharide glycoside derivatives has not been reported.

SUMMARY OF THE INVENTION

An object of the present invention is to provide a method for producing an α or β maltooligosaccharide glycoside derivatives in substantially pure form. Another object of the invention is to provide a method for producing α or β maltooligosaccharide glycoside derivatives of p-nitrophenol or 4-methylumbelliferone.

Accordingly, disclosed herein is a method for producing an α or β maltooligosaccharide glycoside derivative in substantially pure form, comprising incubating an aqueous solution of a glucosyl donor and a glucosyl acceptor in the presence of glucano-transferase enzyme (E.C.2.4.1.19) under transglycosylating conditions to form a reaction mixture containing the maltooligosaccharide glycoside derivative; and separating the maltooligosaccharide glycoside derivative from the reaction mixture.

DETAILED DESCRIPTION OF THE INVENTION

The present invention is based upon the transferase activity of the enzyme, glucanotransferase (E.C.2.4.1.19). This enzyme can be isolated from a variety of sources, and enzymes derived from the organisms *Bacillus macerans*, *Bacillus stearothermophilus*, *Bacillus megaterium*, and *Klebsiella pneumoniae* have been used. The process of the invention is represented by the following formula:

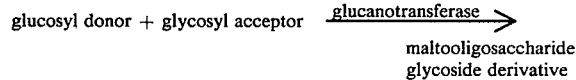

glucosyl donor + glycosyl acceptor $\xrightarrow{\text{glucanotransferase}}$ maltooligosaccharide glycoside derivative The glycosyl donor is generally a cyclic, linear, or branched maltooligosaccharide and preferably includes α-cyclic dextrin, linear maltooligosacharides (for instance, as described by Hall, L. M., U.S. Pat. No. 4,081,326), soluble starch, dextrins, and glycogen. α-cyclic dextrin is the preferred glucosyl donor, in that its use results in high yields of the desired derivatives. According to the general reaction given, the initial reaction product would be dependent upon the specific glucosyl donor used, but because of homologizing reactions, the initial reaction product is rapidly transformed into larger and smaller chain maltooligosaccharides. These homologolizing reactions are counter-productive to the production of a specific α or β oligosaccharide glycoside in high yield. In accordance with the present invention, it has been found that by controlling reactant and enzyme concentrations, and reaction times within specific limitations, the reaction unexpectedly produces the desired maltooligosaccharide glycoside derivative in high yield. Although formation of desired derivatives occur at concentrations of the glucosyl donor of from about 0.01 to about 1 gram per ml of incubation mixture, it is preferable that the concentration be between about 0.10 and about 0.5 grams per ml, depending upon the derivative being prepared and the glucosyl donor being used. For instance, when the glucosyl donor is α-cyclic dextrin, the preferred concentration is from about 0.10 to about 0.25 grams per ml. The higher concentrations are especially preferred for the preparation of the maltoheptaoside glycoside derivatives, as the yield is greatly dependent upon the concentration of the α-cyclic dextrin.

Generally, any chromogenic or fluorogenic compound which can be reacted with glucose to form a glycoside which is subject to enzymatic cleavage can be used to prepare the glucosyl acceptors of the present invention. Representative of such glycosides are the nitrophenyl, 4-methylumbelliferyl, phenolphthalyl and other such derivatives of glucose. The anomeric configuration of the glucosyl acceptor will determine the anomeric configuration of the resulting maltooligosaccharide glycoside derivative, and the preferred glucosyl acceptors are p-nitrophenyl-α-D-glycoside, p-nitrophenyl-β-D-glycoside, 4-methylumbelliferyl-α-D-glycoside, and 4-methylumbelliferyl-β-D-glycoside. Other glucosyl acceptors include the α or β glycosides of maltose, maltotriose, and maltotetraose. Again, the concentration of the glucosyl acceptor influences the yield of the desired maltooligosaccharide derivative. Although formation of the desired maltooligosaccharide glycoside derivatives occurs at concentrations of glucosyl acceptor which are less than the solubility limit in the incubation mixture, it is preferable to employ the glucosyl acceptors in saturated solution. Thus, in the incubation mixture, it is preferable to use the glucosyl acceptors at concentrations of from about 0.5 to about 100 milligrams per ml, depending upon the glucosyl acceptor being used and the concentration of the glucosyl donor. When p-nitrophenylglucoside acceptors are used, the concentration generally ranges from 13 to about 26 milligrams per ml, depending upon the glucosyl donor concentration, and when 4-methylumbelliferyl derivatives are employed, the concentration generally ranges from about 1.5 to about 1.8 milligrams per ml.

The glucanotransferase enzyme is employed in an amount sufficient to catalyze the transfer reaction in a convenient period of time, typically from about 3 minutes to about 5 hours, preferably from about 25 minutes to about 150 minutes of incubation at 40° C. In general, for the procedures described, it is preferable to have present an amount equal to from about 0.3 units up to about 3.0 units of activity (as hereinafter described) per ml of reaction mixture, depending upon the particular derivative which is being prepared. The glucanotransferase enzyme is prepared and purified in such a manner as to be substantially free of hydrolytic activity and is advantageously stable to prolonged storage in solution at 4° C., and is stable for at least 45 minutes at temperatures up to 60° C. at a pH of from 4.9 to 6.0.

The reactants are incubated under transglycosylating conditions for a time sufficient to effect substantial production of the desired product. Included in such conditions are pH, temperature, and reaction time. The pH of the reaction mixture is maintained from about 4.9 up to about 6.0, preferably from about 5.2 to 5.4. Any suitable buffer may be employed in the incubation mixture which adequately controls the pH in the specified region. Sodium or potassium acetate buffers are preferable. The concentration of buffer is generally from about 0.01 to about 0.20 M, preferably from about 0.01 to about 0.08 M. The temperature of the reaction mixture may be from about 10° C. up to about 60° C., preferably between about 40° C. and about 45° C. At the lower temperatures, the solubility of the glucosyl acceptors and donors is decreased thus resulting in lower yields of the desired derivative. At higher temperatures, significant non-enzymatic hydrolysis of the glycoside bond may occur, thus decreasing the yield. Above about 60° C., denaturation of the glucanotransferase enzyme may occur.

The reaction is generally conducted in aqueous solutions, however, the reaction solutions may contain minor concentrations of non-deleterious water-miscible organic solvents, such as ethanol, acetone, dioxane, and the like. The incorporation of such water miscible organic solvents may be used to increase the solubility of one or more reactants.

After completion of the reaction, the reaction is terminated by any suitable means. For example, the reaction may be terminated by denaturation of the glucanotransferase enzyme by adjustment of the pH of the incubation mixture to about 1.8 to about 2.5, preferably to about 2.0 to about 2.1, using any suitable mineral acid, and heating rapidly to 80° C. to 85° C. After about 2 to 3 minutes at this temperature, the mixture is chilled rapidly to room temperature.

Isolation of the desired maltooligosaccharide glycoside derivative from the reaction mixture may be accomplished by a variety of techniques. For instance, the derivative may be separated by precipitation with organic solvents, absorption or partition chromatography, selective crystallization, preparative HPLC, gel filtration chromatography, or other conventional separation techniques.

The following isolation technique has been used for reaction mixtures wherein the glucosyl donor was $\alpha$ or $\beta$-cyclic dextrin, and the glucosyl acceptor was the p-nitrophenyl or 4-methylumbelliferyl glycosides:

1. The pH of the mixture is adjusted to 6–7 with sodium hydroxide and from 0.08 up to 0.20, preferably 0.12 ml of 1,1, 2,2-tetrachloroethane per ml of incubation mixture is added. The mixture is stirred vigorously for approximately 18 hours at 4° C. to precipitate unreacted $\alpha$-cyclic dextrin. Other chlorinated hydrocarbons may be used as precipitants, but tetrachloroethane is preferable as it is more effective. 2. Precipitated $\alpha$-cyclic dextrin is removed from the mixture, e.g., by filtration or centrifugation, and the filtrate or supernatant is deionized by passage through an adequate amount of a conventional mixed-bed ion-exchange resin, such as Amberlite ® MB 3 resin. The effluent from the ion exchange column is evaporated to dryness, preferably by lyophilization. 3. Separation of the desired derivative from the reaction mixture may be achieved by conventional partition chromatography or by other chromatographic separation techniques. A convenient method is to dissolve the dried reaction mixture in water (or alcohol-water 50–60% V/V) and apply the sample to a column of microcrystalline cellulose equilibrated with 85:15 V/V 95% ethanol:water. Smaller maltooligosaccharide glycoside derivatives are eluted by washing with 85% ethanol and may be collected. The maltoheptaoside derivatives are eluted with 70% ethanol, and the product collected. 4. After removal of ethanol by evaporation in vacuo, the syrup is dissolved in water and lyophilized. Yields of maltoheptaoside derivatives produced and isolated by this technique range from about 25–30% of theoretical, based upon the amount of glucosyl acceptor used in the reaction.

Having generally described the invention, a more complete understanding can be obtained by reference to certain specific examples, which are included for illustrative purposes only and are not intended to be limiting unless otherwise specified.

In the examples, the materials and analytical techniques used were as follows. Determination of oligosaccharide derivatives by high performance liquid chromatography (HPLC): Separation was achieved using a Laboratory Data Control liquid chromatograph equipped with a Carbohydrate column (Wates Associates, P/N L84038). The instrument was programmed for an exponentially increasing flow from 1.0 ml/min. to 4.0 ml/min during 10 min elution using the Exp 3 setting. The derivatives were eluted with 78:22 V/V acetonitrile:$H_2O$. Peak heights at 280 nm were proportional to the height of a given compound, but the peak height for different compounds were not equivalent. The amount of compound corresponding to give peak height was determined by collecting the various peaks and determining the amount of p-nitrophenol or of 4-methylumbelliferone in the peak.

Assay of glucanotransferase enzyme: The activity was determined by a modification of the method of Hale and Rawlins (Cereal Chem. 28, 49, 1951) calcium acetate-acetic acid buffer, 0.50 ml, pH 5.2, and 5.0 ml of a 0.50% soluble starch solution (Lintner) was brought to 40° C. and 2.0 ml of a sample suitably diluted with water was added. After incubation for 20 min, 0.20 ml of the incubate was withdrawn and added to a mixture containing 2.5 ml of 0.035 M $I_2$ in 0.25 M KI, and 0.10 ml of 0.10 M $H_2SO_4$. After dilution with 5.0 ml of $H_2O$ the absorbance was determined at 660 nm. A reagent blank consisting of starch, buffer, and $H_2O$ rather than glucanotransferase was included. The difference in absorbance between the reagent blank and the incubation containing the glucanotransferase was proportional to the enzyme activity. A Unit of activity is defined as that amount of glucanotransferase which will cause a decrease in absorbance of 1.00 when measured during zero-order kinetics.

EXAMPLE I

This experiment was designed to determine the preferred ranges of glucosyl donor concentration, glucosyl acceptor concentration and reaction time for the maximum yield of the p-nitrophenyl maltoheptaoside. In the experiment, $\alpha$cyclic dextrin and p-nitrophenyl-$\alpha$-D-glycoside were dissolved in 9.5 ml of 0.077 M sodium acetate buffer, pH 5.2 containing 8 units of glucanotransferase isolated from Bacillus macerans, and the incubation was conducted at 40° C. Samples were taken at the intervals indicated on Table 1, the oligosaccharides were separated by HPLC, and the amounts of the maltooligosaccharides formed in such intervals were determined. The results of the experiment indicate that the yield of maltoheptaoside is highly dependent upon the reactant concentrations and the reaction time.

TABLE 1

| MALTO-OLIGOSAC-CHARIDE DERIVATIVE (mg)* | TIME | | | | | | |
|---|---|---|---|---|---|---|---|
| | 5' | 10' | 20' | 30' | 45' | 60' | 270' |
| A. 750 mg $\alpha$-cyclic dextrin; 40 mg p-$NO_2$-phenylglycoside | | | | | | | |
| $G_4$ | .25 | .67 | 1.2 | 2.1 | 2.7 | 2.9 | |
| $G_5$ | .73 | 1.2 | 2.4 | 3.0 | 4.0 | 4.2 | |
| $G_6$ | .17 | 1.2 | 2.5 | 3.0 | 3.4 | 3.7 | |
| $G_7$ | 24.5 | 40.3 | 53.3 | 54.7 | 48.4 | 37.4 | |
| B. 750 mg $\alpha$-cyclic dextrin; 80 mg p-$NO_2$-phenylglycoside | | | | | | | |
| $G_4$ | .59 | 1.0 | 1.7 | 2.9 | 4.6 | 6.7 | 18 |
| $G_5$ | .36 | 1.8 | 4.6 | 6.3 | 9.7 | 12.7 | 21.6 |

TABLE 1-continued

| MALTO-OLIGOSAC-CHARIDE DERIVATIVE (mg)* | \multicolumn{7}{c}{TIME} |
|---|---|---|---|---|---|---|---|
| | 5' | 10' | 20' | 30' | 45' | 60' | 270' |
| $G_6$ | .34 | 1.4 | 3.4 | 5.6 | 10.5 | 11.9 | 19.5 |
| $G_7$ | 31.7 | 53.3 | 85 | 96.5 | 102 | 102 | 35.1 |
| C. 750 mg α-cyclic dextrin; 160 mg p-NO$_2$-phenylglycoside | | | | | | | |
| $G_4$ | .84 | 1.2 | 2.4 | 3.5 | 5.8 | 9.2 | |
| $G_5$ | 1.2 | 2.4 | 5.2 | 7.9 | 13.0 | 19.2 | |
| $G_6$ | .85 | 1.6 | 4.2 | 6.4 | 10.8 | 15.6 | |
| $G_7$ | 31.7 | 49.5 | 80.6 | 90 | 107 | 115 | |
| D. 325 mg α-cyclic dextrin; 80 mg p-NO$_2$-phenylglycoside | | | | | | | |
| $G_4$ | .42 | 1.0 | 3.4 | 5.7 | 6.7 | 9.4 | |
| $G_5$ | 1.5 | 3.6 | 8.3 | 9.7 | 14.7 | 19.2 | |
| $G_6$ | 1.2 | 12.4 | 5.8 | 7.6 | 11.0 | 13.5 | |
| $G_7$ | 24.5 | 40.3 | 49.0 | 49.0 | 46.1 | 43.2 | |
| E. 1500 mg α-cyclic dextrin; 80 mg p-NO$_2$-phenylglycoside | | | | | | | |
| $G_4$ | .59 | .67 | .83 | 1.5 | 2.4 | 4.2 | |
| $G_5$ | .97 | 1.1 | 1.8 | 3.3 | 4.7 | 6.1 | |
| $G_6$ | .34 | .50 | 1.35 | 2.54 | 4.2 | 4.1 | |
| $G_7$ | 26.5 | 51.8 | 78.3 | 97.3 | 117 | 115 | |

*The abbreviations $G_4$–$G_7$ indicate the maltooligosaccharide derivatives with 4 to 7 glucosyl units, respectively.

EXAMPLE II

Preparation of pNO$_2$-phenyl-α-D-maltoheptaoside

Reaction conditions were chosen to give high yields of the desired p-NO$_2$-phenyl-α-D-maltoheptaoside. Incubation of 15.0 g of α-cyclic dextrin, 1.60 g of p-NO$_2$-phenyl-α-D-glycoside, and 156 units of glucanotransferase from *Bacillus macerans* in 60 ml of 0.083 M sodium acetate buffer, pH 5.2, was continued for 25 min at 40° C. The pH of the reaction mixture was adjusted to 2.0 with 1.0 M HCl, the acidified mixture was heated to 80°–82° C. for 2 min and cooled to room temperature. After adjustment of the pH to 6–7 with 1.0 M NaOH 7.0 ml of 1,1,2,2-tetrachloroethane was added to precipitate excess α-cyclic dextrin. The mixture was stirred at 40° C. for 18 hr, the precipitate was removed by filtration, and the filtrate was deionized by passage through a 60 ml bed volume of Amerberlite®-MB-3resin. The ion exchange resin was washed with H$_2$O to obtain complete recovery of the desired product. The solution was lyophilized. Separation of the p-NO$_2$-phenyl-α-D-maltoheptaoside from the dried mixture was conveniently accomplished by partition chromatography on a column of microcrystalline cellulose (Sigmacell® Type 50), 2.5×45 cm. The column was equilibrated with 85:15 V/V 95% ethanol:H$_2$O, and the sample dissolved in 10 ml of 60% ethanol was applied to the column. The column was washed with 85% ethanol:H$_2$O to remove unreacted p-NO$_2$-phenyl-α-D-glycoside and other contaminating p-NO$_2$-phenyl-α-D-glycosides formed by the action of glucanotransferase. The desired product, p-NO$_2$-phenyl-α-D-maltoheptaoside was eluted from the column by 70% ethanol:H$_2$O. The compound was collected, ethanol was removed by evaporation in vacuo, the syrup was dissolved in H$_2$O and lyophilized. Yield of p-NO$_2$-phenyl-α-D-maltoheptaoside was 1.60 gm. The purity of the compound by HPLC was in excess of 95%.

EXAMPLE III

Preparation of p-NO$_2$-phenyl-β-D-maltoheptaoside

Reaction conditions were chosen to give high yields of the desired p-NO$_2$-phenyl-α-D-maltoheptaoside. Incubation of 9.4 g of α-cyclic dextrin, 0.80 g of p-NO$_2$-phenyl-β-glycoside, and 64 units of glucanotransferase from *Bacillus macerans* in 60 ml of 0.083 M sodium acetate buffer, pH 5.2 was continued for 30 min. Isolation of the desired product was accomplished by the procedures and techniques described in Example II. Yield of p-NO$_2$-phenyl-β-maltoheptaoside was 0.60 g. Purity by HPLC was in excess of 95%.

EXAMPLE IV

Preparation of 4-methylumbelliferyl-α-D-maltoheptaoside

Reaction conditions were chosen to give high yields of the desired 4-methylumbelliferyl-α-D-maltoheptaoside. Incubation of 26.0 g of αcyclic dextrin, 0.467 g of 4-methylumbelliferyl-α-D-glycoside, and 71 units of glucanotransferase from *Bacillus macerans* in 260 ml of 0.01 M sodium acetate buffer, pH 5.2, was continued for 45 min at 40° C. Isolation of the desired product was accomplished by the procedures and techniques described in Example II. Yield of 4-methylumbelliferyl-α-D-maltoheptaoside was 0.576 g. The purity of HPLC was in excess of 95%.

EXAMPLE V

Preparation of 4-methylumbelliferyl-β-D-maltoheptaoside

Reaction conditions are chosen to give high yields of the desired 4-methylumbelliferyl-β-D-maltoheptaoside. Incubation of 26 g of α-cyclic dextrin, 0.467 g of 4-methylumbelliferyl-β-D-glycoside, and 71 Units of glucanotransferase from *Bacillus macerans* in 260 ml of 0.01 M sodium acetate buffer, pH 5.2, is continued for 45 min at 40° C. Isolation of the desired product is accomplished by the procedures and techniques described in Example II. The example should yield 4-methylumbelliferyl-β-D-maltoheptoaside in high purity.

EXAMPLE VI

Simultaneous preparation of phenolphthalyl-α-D-maltopentaoside and phenolphthalyl-α-D-maltotetraoside Reaction conditions are chosen to give high yields of the desired maltooligosaccharide glycoside derivatives. Incubation of 0.5 g of linear oligosaccharide (DP-5 to DP-10, as discussed by L. M. Hall, U.S. Pat. No. 4,081,326), 0.08 g of phenolphthalyl-α-D-glycoside, and 8 units of glucanotransferase from *Bacillus stearothermophilus* in 5.0 ml of 0.10 M sodium acetate buffer, pH 5.2, is continued for 110 min at 40° C. Following denaturation of the enzyme, isolation of the desired products is accomplished' by partition chromatography as described in Example II. The experiment should yield approximately equal quantities of phenolphthalyl-α-D-maltopentaoside and phenolphthalyl-α-D-maltotetraoside in high purity.

EXAMPLE VII

Preparation of *Bacillus macerans* amylase

A culture of *Bacillus macerans* (ATCC 8517) in 2000 ml of H$_2$O containing 2% CaCO$_3$ and 10% wet weight of potato slices was maintained at 38° C. to 40° C. for four weeks. The culture was centrifuged at 5000 xg and adjusted to 90% saturation with ammonium sulfate at 4° C. The precipitate was collected by centrifugation, dissolved in 0.02 M piperazine-HCl buffer, pH 6.2 to a final volume of 75 ml. The amylase was precipitated at 35% saturation of ammonium sulfate, dissolved in 13 ml of piperazine buffer (0.02 M, pH 6.2) and dialyzed vs the same buffer for 24 hours. The dialyzed sample was applied to DEAE cellulose, 2.5×45 cm, equilibrated with the 0.02 M piperazine buffer. The enzyme was eluted from the DEAE by 500 ml of a linear gradient of 0.02 M to 0.52 M Cl$^-$ using NaCl in the 0.02 M piperazine buffer, pH 6.2. Fractions containing enzymatic activity were combined and used in preceding examples I-V. There was no detectasble hydrolytic activity in the resulting enzyme product.

EXAMPLE VIII

This experiment was conducted to determine the utility of substrates produced by the present method in the amylase assay procedures described by Driscoll, et al. in U.S. Pat. No. 4,102,747. Amylase activity was measured in a test solution containing the following components: phosphate buffer 0.1 M, pH 7.1; NaCl 0.05 M; Maltase (prepared in accordance with Hall, L. M. U.S. Pat. No. 4,071,407), 300 Units/ml; and p-Nitrophenyl-α-D-maltoheptaoside, 2.5 mg/ml.

Amylase activity was detected at 405 nm at 37° C. Amylase activity was expressed as the rate of change of absorbance per minute resulting from the formation of p-nitrophenol caused by the enzymatic action of amylase on the substrate. The rate of formation of p-nitrophenol in the absence of amylase was insignificant. Sixty-seven serum samples were analyzed by the foregoing procedure and also by the α-Amyl Amylase procedure (available from the Dade Division of American Hospital Supply Corporation). Correlation between the two methods was excellent, with a correlation coefficient (r) of 0.969.

I claim:

1. A method for producing an α or β maltooligosaccharide glycoside derivative in substantially pure form, comprising incubating an aqueous solution of a glucosyl donor and a chromogenic or fluorogenic glycoside in the presence of a glucanotransferase enzyme (E.C.2.4.1.19) under transglycosylating conditions to form a reaction mixture containing the maltooligosaccharide glycoside derivative; and separating the maltooligosaccharide glycoside derivative from the reaction mixture.

2. The method of claim 1 wherein the glucosyl donor is selected from the group consisting of α-cyclic dextrin, β-cyclic dextrin, linear oligosaccharides, maltotriose, maltotetraose, maltopentaose, maltohexaose, maltoheptaose, starch, glycogen and dextrins; the chromogenic or fluorogenic gylcoside is selected from the group consisting of p-nitrophenyl-α-D-glycoside, p-nitrophenyl-β-D-glycoside, 4-methylumbelliferyl-α-D-glycoside, 4-methylumbelliferyl-β-D-glycoside.

3. The method of claims 1 or 2 wherein the glucanotransferase enzyme is an enzyme produced by an organism selected from the group consisting of *Bacillus macerans, Bacillus stearothermophilus, Bacillus megaterium,* and *Klebsiella pneumoniae.*

4. The method of claims 1 or 2 wherein the transglycoslating conditions include a pH of from about 4.9 to about 6.0, a reaction temperature of from about 10° C. to about 60° C., and a reaction time from about 3 minutes to about 5 hours.

5. The method of claims 1 or 2 wherein the transglycosolating conditions include a pH of from about 5.2 to about 5.4, a reaction temperature of from about 38° C. to about 45° C., and a reaction time of from about 25 minutes to about 150 minutes.

6. The method of claim 4 wherein the glucosyl donor is α-cyclic dextrin, and is employed in a concentration of from about 0.10 to about 0.25 grams per ml, the chromogenic or fluorogenic glycoside is selected from the group consisting of p-nitrophenyl-α-D-glycoside, p-nitrophenyl-β-D-glycoside, 4-methylumbelliferyl-α-D-glycoside, and 4-methylumbelliferyl-β-D-glucoside, and is employed at a concentration of from about 1.5 to about 26 milligrams per ml, and the glucanotransferase enzyme is an enzyme produced by the organism *Bacillus macerans* and is employed at a concentration sufficient to catalyze the reaction.

7. The method of claim 5 wherein the glucosyl donor is α-cyclic dextrin, and is employed in a concentration of from about 0.10 to about 0.25 grams per ml, the chromogenic or fluorogenic glycoside is selected from the group consisting of p-nitrophenyl-α-D-glycoside, p-nitrohenyl-β-D-glycoside, 4-methylumbelliferyl-α-D-glycoside, and 4-methylumbelliferyl-β-D-glycoside, and is employed at a concentration of from about 1.5 to about 26 milligrams per ml, and the glucanotransferase enzyme is an enzyme produced by the organism *Bacillus macerans* and is employed at a concentration of about 0.3 Units to about 3.0 Units of activity per ml of reaction mixture.

8. The method of claims 1 or 2 wherein the glucosyl donor is α-cyclic dextrin and the maltooligosaccharide glycoside derivative is separated from the reaction mixture by the steps of:

a. denaturing the glucanotransferase by adjusting the pH of the reaction mixture to about 1.8 to 2.5, heating rapidly to 80° C. to 85° C. and, after about 2 to 3 minutes, chilling rapidly to room temperature;

b. adjusting the pH of the reaction mixture to about 6 to 7 and adding about 0.08 to about 0.20 ml of a liquid chlorinated hydrocarbon, then stirring for about 18 hours at about 4° C., to precipitate unreacted α-cyclic dextrin;

c. removing the precipitated α-cyclic dextrin from the reaction mixture thereby forming a clarified reaction mixture;

d. chromatographically separating the maltooligosaccharide glycoside derivative from the clarified reaction mixture on a microcrystalline cellulose column using ethanol-water eluates;

e. collecting the maltooligosaccharide glycoside-containing fractions; and f. evaporating the collected fractions to dryness.

* * * * *